United States Patent [19]

Ota et al.

[11] Patent Number: 5,705,651
[45] Date of Patent: Jan. 6, 1998

[54] PROCESS FOR PRODUCING A 3,4-ALKYLENE-1,3,4-THIADIAZOLIDIN-2-ONE AND INTERMEDIATES FOR THE SAME

[75] Inventors: Chikako Ota; Bunji Natsume, both of Kanagawa, Japan

[73] Assignee: Mitsubishi Chemical Corporation, Tokyo, Japan

[21] Appl. No.: 517,676

[22] Filed: Aug. 22, 1995

[30] Foreign Application Priority Data

Aug. 22, 1994 [JP] Japan .................................. 6-196873

[51] Int. Cl.$^6$ .................. C07D 401/00; C07D 285/12
[52] U.S. Cl. .............................................. 548/126
[58] Field of Search ................................. 548/126

[56] References Cited

FOREIGN PATENT DOCUMENTS 0 273 417  7/1988  European Pat. Off. .
WO 92/21684  12/1992  WIPO .
WO 95/06643  3/1995  WIPO .

OTHER PUBLICATIONS

Wikel et al., J. Org. Chem. vol. 39, No. 24 (1974), pp. 3506–3508.

Molina et al., Synthesis, No. 12 (1989) pp. 923–929.

Lissamma et al., Chemical Abstracts, vol. 106, No. 3, 19 Jan. 1987 Abstract 18448u.

*Primary Examiner*—Johann Richter
*Attorney, Agent, or Firm*—Wenderoth, Lind & Ponack

[57] ABSTRACT

According to the process of the present invention, a 3,4-alkylene-1,3,4-thiadiazolidin-2-one, which is useful as a herbicide, can be easily produced in a high yield by reacting a 1,3,4-thiadiazolidin-2-one with a dihaloalkane in the presence of a base.

12 Claims, No Drawings

PROCESS FOR PRODUCING A 3,4-ALKYLENE-1,3,4-THIADIAZOLIDIN-2-ONE AND INTERMEDIATES FOR THE SAME

FIELD OF THE INVENTION

This invention relates to a process for producing a 3,4-alkylene-1,3,4-thiadiazolidin-2-one which is useful as a herbicide.

BACKGROUND OF THE INVENTION

Well-known processes for producing a 3,4-alkylene-1,3,4-thiadiazolidin-2-one include a process comprising reacting hexahydropyridazine with an isothiocyanate and treating the thiourea thus obtained with phosgene to thereby synthesize 3,4-tetramethylene-1,3,4-thiadiazolidin-2-one (JP-A-63-264489; the term "JP-A" as used herein means an "unexamined published Japanese patent application") (corresponding to U.S. Pat. No. 4,906,279), and a process comprising synthesizing 3,4-trimethylene-1,3,4-thiadiazolidin-2-one with the use of tetrahydropyrazole as a starting material (International Patent Application WO-9221684).

However, these methods have some disadvantages such that a complicated process is required for producing hexahydropyridazine or tetrahydropyrazole to be used as the starting material and that since these compounds per se are liable to be oxidized in the atmosphere and have low boiling points, problems occur in handling properties.

SUMMARY OF THE INVENTION

As a result of extensive investigation to solve the above-mentioned problems, the present inventors have found a process for easily and efficiently producing a 3,4-alkylene-1,3,4-thiadiazolidin-2-one in a high yield with the use of a 1,3,4-thiadiazolidin-2-one as a starting material, thus completing the present invention.

Accordingly, the present invention relates to a process for producing 3,4-alkylene-1,3,4-thiadiazolidin-2-one represented by the formula (III):

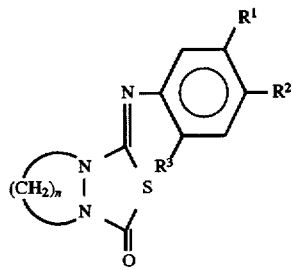

wherein $R^1$ represents a hydrogen atom or an inert substituent; $R^2$ represents a halogen atom, a nitro group, a methyl group or a methoxy group; $R^3$ represents a hydrogen atom or a halogen atom; and n represents an integer of from 3 to 5, which comprises reacting a 1,3,4-thiadiazolidin-2-one represented by the formula (I):

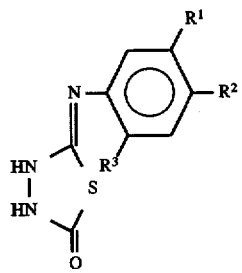

wherein $R^1$, $R^2$ and $R^3$ are each as defined above, with a dihaloalkane represented by the formula (II):

wherein X represents a halogen atom; and n is as defined above, in the presence of a base.

The present invention further relates to the following aspects: that the 1,3,4-thiadiazolidin-2-one is obtained by hydrolyzing a 3-formyl-1,3,4-thiadiazolidin-2-one represented by the following formula (IV), which is a novel compound:

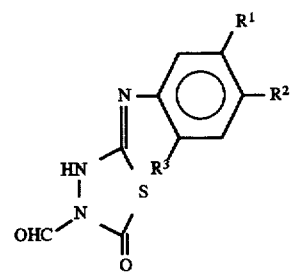

wherein $R^1$, $R^2$ and $R^3$ are each as defined above; that the 3-formyl-1,3,4-thiadiazolidin-2-one is obtained by reacting a thiosemicarbazide represented by the following formula (V), which is a novel compound:

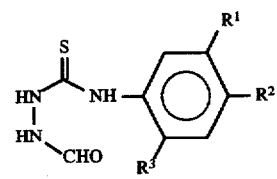

wherein $R^1$, $R^2$ and $R^3$ are each as defined above, with phosgene; and that the thiosemicarbazide is obtained by reacting an isothiocyanate represented by the following formula (VI):

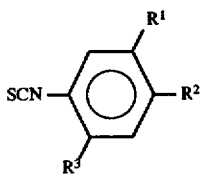

wherein $R^1$, $R^2$ and $R^3$ are each as defined above, with formhydrazide.

DETAILED DESCRIPTION OF THE INVENTION

Now, the present invention will be described in detail below.

In the formulae (I) and (III) to (VI), the term "inert substituent" in $R^1$ means a substituent which is inert against the reaction of synthesizing a 3,4-alkylene-1,3,4-thiadiazolidin-2-one of the formula (III) from a 1,3,4-thiadiazolidin-2-one of the formula (I). Moreover, it means a substituent which is inert against a series of reactions of synthesizing a 1,3,4-thiadiazolidin-2-one of the formula (I) from an isothiocyanate of the formula (VI).

Typical examples of the inert substituent include a hydrogen atom, a group represented by —A—$R^6$ and a group represented by —CO—$R^7$. A represents an oxygen atom or a sulfur atom. $R^6$ represents an alkyl group having 1 to 4 carbon atoms, an alkenyl group having 2 to 4 carbon atoms, an alkynyl group having 2 to 4 carbon atoms, a cycloalkyl group having 3 to 6 carbon atoms, a haloalkyl group having 1 to 4 carbon atoms, a haloalkenyl group having 2 to 4 carbon atoms, a cyanoalkyl group having 2 to 5 carbon atoms, an alkoxyalkyl group having 2 to 6 carbon atoms, an oxoalkyl group having 3 to 6 carbon atoms or a group represented by —B—$COR^8$. B represents a straight-chain or branched alkylene group having 1 to 5 carbon atoms. $R^8$ represents —$OR^9$, —$SR^{10}$ or —$NR^{11}R^{12}$. $R^9$ and $R^{10}$ each represents an alkyl group having 1 to 4 carbon atoms, an alkenyl group having 2 to 4 carbon atoms, an alkynyl group having 2 to 4 carbon atoms, a cycloalkyl group having 3 to 6 carbon atoms, a haloalkyl group having 1 to 4 carbon atoms, a cyanoalkyl group having 2 to 5 carbon atoms, an alkoxyalkyl group having 2 to 6 carbon atoms, a phenyl group, a benzyl group or a 3- to 6-membered heterocyclic group having 1 to 3 hetero atoms selected from the group consisting of oxygen atom, sulfur atom and nitrogen atom. $R^{11}$ and $R^{12}$ independently each represents a hydrogen atom, an alkyl group having 1 to 4 carbon atoms, an alkenyl group having 2 to 4 carbon atoms, an alkynyl group having 2 to 4 carbon atoms, a cycloalkyl group having 3 to 6 carbon atoms, a haloalkyl group having 1 to 4 carbon atoms, a cyanoalkyl group having 2 to 5 carbon atoms, an alkoxyalkyl group having 2 to 6 carbon atoms, a phenyl group, a benzyl group, a 3- to 6-membered heterocyclic group having 1 to 3 hetero atoms selected from the group consisting of oxygen atom, sulfur atom and nitrogen atom, or an alkoxy group having 1 to 4 carbon atoms. The group represented by —$NR^{11}R^{12}$ may form a 3-to 6-membered heterocyclic group having 1 or 2 nitrogen atoms and 0 or 1 oxygen atom which may be substituted by 1 or 2 methyl groups. $R^7$ has the same meaning as that of $R^8$. When $R^9$, $R^{10}$, $R^{11}$ and $R^{12}$ each represents a phenyl group, a benzyl group or a heterocyclic group, these phenyl, benzyl and heterocyclic groups each may be further substituted by a halogen atom, an alkyl group having 1 to 4 carbon atoms, a trifluoromethyl group, an alkoxy group having 1 to 4 carbon atoms, a haloalkoxy group having 1 to 4 carbon atoms, an acyloxy group having 2 to 5 carbon atoms, an alkylthio group having 1 to 4 carbon atoms, an alkylsulfonyl group having 1 to 4 carbon atoms, a nitro group, a cyano group or an alkoxycarbonyl group having 2 to 5 carbon atoms.

Preferable compounds of the formulae (I) and (III) to (VI) according to the present invention are compounds wherein $R^1$ is a group represented by —$ACH_2CO_2R^4$, in which A represents an oxygen atom or a sulfur atom and $R^4$ represents an alkyl group having 1 to 4 carbon atoms (for example, methyl, ethyl, propyl, isopropyl, butyl, isobutyl, sec-butyl or tert-butyl), a cycloalkyl group having 3 to 6 carbon atoms (for example, cyclopropyl, cyclobutyl, cyclopentyl or cyclohexyl) or a tetrahydrofuryl group substituted by an acyloxy group having 2 to 5 carbon atoms (for example, acetyloxy, propionyloxy, butyryloxy, isobutyryloxy, valeryloxy, isovaleryloxy, pivaloyloxy, acryloyloxy, propioloyloxy, methacryloyloxy or crotonoyloxy); $R^2$ is a halogen atom (for example, fluorine, chlorine, bromine or iodine); $R^3$ is a hydrogen atom or a halogen atom; and n is an integer of from 3 to 5. A more preferable compound is a compound wherein $R^1$ is a group represented by —$SCH_2CO_2R^4$, in which $R^4$ represents a methyl group or a 4-acetoxytetrahydrofuran-3-yl group; $R^2$ is a chlorine atom; $R^3$ is a fluorine atom; and n is 3 or 4.

The 3,4-alkylene-1,3,4-thiadiazolidin-2-one of the formula (III) can be obtained in the following manner, to a solution of the 1,3,4-thiadiazolidin-2-one of the formula (I), adding the dihaloalkane of the formula (II) in an amount 1 to 1.2 times by mol as much as that of the 1,3,4-thiadiazolidin-2-one in the presence of a base in an amount of 2 to 3 times by mol as much as that of the 1,3,4-thiadiazolidin-2-one, allowing the mixture to react at a temperature ranging from about 10° to 200° C. preferably from 10° to 100° C. for about 0.5 to 24 hours to thereby complete alkylation, and then removing the solvent. The 3,4-alkylene-1,3,4-thiadiazolidin-2-one thus obtained can be purified by, for example, recrystallization or column chromatography.

Examples of the dihaloalkane of the general formula (II) to be used in the present invention include 1,3-dichloropropane, 1,3-dibromopropane, 1,3-diiodopropane, 1,4-dichlorobutane, 1,4-dibromobutane, 1,4-diiodobutane, 1,5-dichloropentane, 1,5-dibromopentane and 1,5-diiodopentane.

Examples of the base to be used in the present invention include inorganic bases such as sodium hydrogencarbonate, potassium hydrogencarbonate, sodium carbonate, potassium carbonate, sodium hydroxide, potassium hydroxide, sodium methylate, sodium ethylate and sodium hydride. It is particularly preferable to use potassium carbonate or sodium carbonate therefor.

Examples of the solvent to be used in the present invention include aromatic hydrocarbons such as benzene, toluene or xylene, halogenated hydrocarbons such as dichloromethane, chloroform or 1,2-dichloroethane, ethers such as diethyl ether, tetrahydrofuran or dioxane, esters such as methyl acetate or ethyl acetate, ketones such as acetone or methyl ethyl ketone, alcohols such as methanol, ethanol or propanol, and polar solvent such as N,N-dimethylformamide, N-methylpyrrolidone, dimethyl sulfoxide, acetonitrile or water.

The 1,3,4-thiadiazolidin-2-one to be used as the starting material may be synthesized in accordance with the following series of reactions, though the origin thereof is not restricted thereto. The compounds of the formulae (I), (IV) and (V) are novel substances.

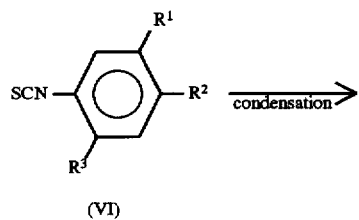

(VI)

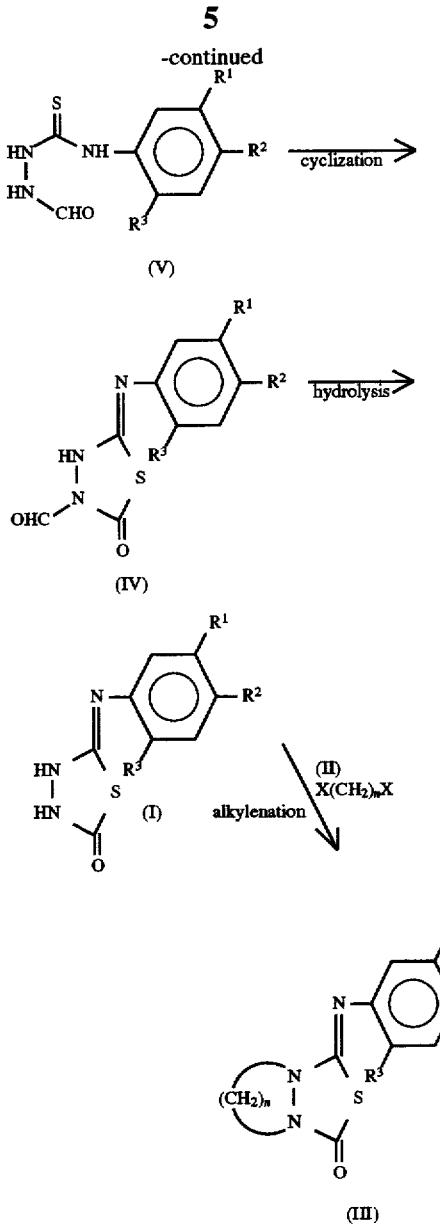

To a solution of an isothiocyanate represented by the above formula (VI), formylhydrazide is added, followed by the condensation. After the completion of the reaction, the reaction mixture is concentrated to thereby give the thiosemicarbazide of the above formula (V). The formylhydrazide is used in an amount 1 to 1.5 times by mol as much as that of the isothiocyanate of the formula (VI). The reaction temperature ranges usually from about 0° to 100° C., preferably from 0° to 50° C. The reaction time ranges from about 0.5 to 24 hours. The thiosemicarbazide thus obtained can be purified by, for example, recrystallization or silica gel column chromatography.

Next, phosgene is added to the solution of the thiosemicarbazide of the formula (V) to thereby perform cyclization. After the completion of the reaction, the reaction mixture is filtered to thereby give the 3-formyl-1,3,4-thiadiazolidin-2-one of the above formula (IV). The phosgene is used in an amount 1 to 1.2 times by mol as much as that of the thiosemicarbazide of the formula (V). The reaction temperature ranges usually from about 0° to 100° C., preferably from 0° to 50° C. The reaction time ranges from about 0.5 to 24 hours. The 3-formyl-1,3,4-thiadiazolidin-2-one of the formula (IV) thus obtained can be purified by, for example, recrystallization or silica gel column chromatography.

Further, an acid is added to the solution of the 3-formyl-1,3,4-thiadiazolidin-2-one of the formula (IV) to thereby perform hydrolysis. After the completion of the reaction, the reaction mixture is concentrated to thereby give the 1,3,4-thiadiazolidin-2-one of the formula (I). Examples of the acid to be used herein include hydrogen chloride, hydrogen bromide and hydrogen iodide. The acid is used in an amount 0.05 to 2 times by mol as much as that of the 3-formyl-1,3,4-thiadiazolidin-2-one of the formula (IV) and water is added in an amount 1 to 1.5 times by mol as much as that of the 3-formyl-1,3,4-thiadiazolidin-2-one. The reaction temperature ranges usually from about 0° to 100° C., preferably from 0° to 50° C. The reaction time ranges from about 0.5 to 24 hours. The 1,3,4-thiadiazolidin-2-one thus obtained can be purified by, for example, recrystallization or silica gel chromatography.

As the solvent employed in the series of reactions, the solvents, which are employed in the reaction for synthesizing the 3,4-alkylene-1,3,4-thiadiazolidin-2-one of the formula (III) from the 1,3,4-thiadiazolidin-2-one of the formula (I), can be used. When an alcohol is used as a solvent, the hydrolysis of the 3-formyl-1,3,4-thiadiazolidin-2-one of the formula (IV) proceeds without adding water. When water is added in an amount of 1 to 1.5 times by mol as much as that of the 3-formyl-1,3,4-triadiazolidin-2-one after the synthesis of the 3-formyl-1,3,4-thiadiazolidin-2-one of the formula (IV), the reaction for synthesizing the 1,3,4 -thiadiazolidin-2-one of the formula (I) can be carried out in succession.

The present invention will now be illustrated in greater detail by way of the following Examples, but should not be construed as being limited thereto.

EXAMPLE 1

Production of N-[5-(4-acetoxytetrahydrofuran-3-yloxycarbonyl-methylthio)-4-chloro-2-fluorophenylaminothiocarbonyl]-N'-formylhydrazine:

A solution of 5-(4-acetoxytetrahydrofuran-3-yloxycarbonylmethylthio)-4-chloro-2-fluorophenyl isothiocyanate (53.5 g, 0.132 mol) in tetrahydrofuran (200 ml) was stirred at room temperature (17° to 23° C.) and formylhydrazide (8.31 g, 0.139 mol) was added thereto in the form of crystals. Then the obtained mixture was stirred at room temperature for 3 hours. After evaporating the solvent, the residue was poured into water, extracted with ethyl acetate (500 ml), washed successively with water and a saturated aqueous solution of sodium chloride, and then dried over anhydrous magnesium sulfate. Next, the solvent was evaporated under reduced pressure, and ethanol (200 ml) and hexane (360 ml) were added to the residue. Thus crystals were forced to precipitate to give the title compound having the following physical properties (60.3 g, yield: 98%).

m.p.: 137.5°–138.4° C.

NMR (δ, DMSO—CDCl₃): 2.07 (s, 3H), 3.74 (s, 2H), 3.8 (m, 2H), 4.1 (m, 2H), 5.3 (m, 2H), 7.18 (d, 1H, J=10 Hz), 8.1 (b, 1H), 8.6 (b, 1H), 9.2 (b, 1H), 9.7 (b, 1H).

EXAMPLE 2

Production of N-[4-chloro-2-fluoro-5-(methoxycarbonylmethyl-thio)phenylaminothiocarbonyl]-N'-formylhydrazine:

By using 5-(methoxycarbonylmethylthio)-4-chloro-2-fluorophenyl isothiocyanate, the same procedure as in the above Example 1 was repeated to give the title compound having the following physical properties (yield: 97%).

m.p.: 157.4°–157.8° C. NMR (δ, CDCl$_3$): 3.71 (s, 2H), 3.74 (s, 3H), 7.18 (d, 1H, J=10 Hz), 8.13 (s, 1H), 8.57 (d, 1H, J=8 Hz), 9.2 (b, 1H), 9.78 (b, 1H), 10.6 (b, 1H).

EXAMPLE 3

Production of 5-[5-(4-acetoxytetrahydrofuran-3-yloxycarbonyl-methylthio)-4-chloro-2-fluorophenylimino]-3-formyl-1,3,4-thiadiazolidin-2-one:

Under ice-cooling, a phosgene-toluene solution (16.6%, 84.6 g, 0.142 mol) was dropped into a solution of N-[5-(4-acetoxytetrahydrofuran-3-yloxycarbonylmethylthio)-4-chloro-2-fluorophenylaminothiocarbonyl]-N'-formylhydrazine (60.0 g, 0.129 mol) in acetone (1200 ml). Thus the precipitation of white crystals began in the course of the addition at 8° to 10° C. Following the addition, the mixture was stirred at room temperature for 1 hour. After the completion of the reaction, hexane (1,000 ml) was added to the mixture, followed by filtration and drying. Thus the title compound having the following physical properties was obtained (57.5 g, yield: 91%).

m.p.: 130.7°–132.3° C. NMR (δ, DMSO—CDCl$_3$): 2.07 (s, 3H), 3.74 (s, 2H), 3.8 (m, 2H), 4.1 (m, 2H), 5.3 (m, 2H), 7.18 (d, 1H, J=10 Hz), 8.1 (b, 1H), 8.6 (b, 1H), 9.2 (b, 1H), 9.7 (b, 1H).

EXAMPLE 4

Production of 5-[4-chloro-2-fluoro-5-(methoxycarbonylmethyl-thio)phenylimino]-3-formyl-1,3,4-thiadiazolidin-2-one:

By using N-[4-chloro-2-fluoro-5-(methoxycarbonylmethylthio)phenylaminothiocarbonyl]-N'-formylhydrazine, the same procedure as in the above Example 3 was repeated to give the title compound having the following physical properties (yield: 84%).

m.p.: 176.4°–177.2° C. NMR (δ, DMSO): 3.62 (s, 2H), 3.92 (s, 3H), 7.62 (d, 1H, J=10 Hz), 8.32 (d, 1H, J=8 Hz), 9.00 (s, 1H), 10.32 (b, 1H).

EXAMPLE 5

Production of 5-[5-(4-acetoxytetrahydrofuran-3-yloxycarbonyl-methylthio)-4-chloro-2-fluorophenylimino]-1,3,4-thiadiazolidin-2-one:

A solution of 5-[5-(4-acetoxytetrahydrofuran-3-yloxycarbonylmethylthio)-4-chloro-2-fluorophenylimino]-3-formyl-1,3,4-thiadiazolidin-2-one (10.0 g, 0.0203 mol) in acetone (300 ml) was stirred at room temperature and a 5% HCl-MeOH solution (14.9 g) was dropped thereinto. After stirring at room temperature for 30 minutes, the solvent was evaporated, and ethanol (50 ml) and hexane (100 ml) were added to the residue. Thus crystals were forced to precipitate to give the title compound having the following physical properties (9.43 g).

m.p.: 130.7°–132.3° C. NMR (δ, DMSO—CDCl$_3$): 2.04 (s, 3H), 3.8 (m, 2H), 3.82 (s, 2H), 4.0 (m, 2H), 5.3 (m, 2H), 7.16 (d, 1H, J=10 Hz), 8.56 (d, 1H, J=9 Hz), 9.04 (s, 1H), 9.9 (b, 1H).

EXAMPLE 6

Production of 5-[4-chloro-2-fluoro-5-(methoxycarbonylmethyl-thio)phenylimino]-1,3,4-thiadiazolidin-2-one:

By using 5-[4-chloro-2-fluoro-5-(methoxycarbonylmethylthio)phenylimino]-3-formyl-1,3,4-thiadiazolidin-2-one, the same procedure as in the above Example 5 was repeated to give the title compound having the following physical properties (yield: 98%).

m.p.: 187.3°–188.2° C. NMR (δ, DMSO): 3.65 (s, 2H), 3.71 (s, 3H), 7.14 (d, 1H, J=10 Hz), 8.29 (d, 1H, J=8 HZ), 8.7 (b, 1H), 11.0 (b, 1H).

EXAMPLE 7

Production of 9-[5-(4-acetoxytetrahydrofuran-3-yloxycarbonyl-methylthio)-4-chloro-2-fluorophenylimino]-8-thia-1,6-diaza-bicyclo[4.3.0]nonan-7-one:

A mixture composed of 5-[5-(4-acetoxytetrahydrofuran-3-yloxycarbonylmethylthio)-4-chloro-2-fluorophenylimino]-thiadiazolidin-2-one (3.00 g, 6.47 mmol), potassium carbonate (2.23 g, 16.2 mmol) and 1,4-dibromobutane (1.68 g, 7.77 mmol) in acetone (30 ml) was refluxed for 2 hours. Then the reaction mixture was filtered and the solvent was evaporated. The residue was poured into water and extracted with ethyl acetate. Next, the organic layer was washed with water thrice and dried over anhydrous magnesium sulfate. Then the solvent was evaporated under reduced pressure and the residue thus obtained was purified by silica gel column chromatography (50% ethyl acetate/hexane) to give the title compound having the following physical properties (2.65 g, yield: 80%).

m.p.: 106.5°–108.0° C. NMR (δ, CDCl$_3$): 1.79–1.97 (m, 4H), 2.04 (s, 3H), 3.65 (s, 2H), 3.72–3.83 (m, 2H), 4.02–4.09 (m, 2H), 5.27–5.37 (m, 2H), 7.12 (d, 1H, J=8 Hz), 7.20 (d, 1H, J=10 Hz).

EXAMPLE 8

Production of 9-[4-chloro-2-fluoro-5-(methoxycarbonylmethyl-thio)phenylimino]-8-thia-1,6-diazabicyclo[4.3.0]nonan-7-one:

By using 5-[4-chloro-2-fluoro-5-(methoxycarbonylmethylthio)phenylimino]-1,3,4-thiadiazolidin-2-one, the same procedure as in the above Example 7 was repeated to give the title compound having the following physical properties.

m.p.: 106.0°–107.0° C. NMR (δ, CDCl$_3$): 1.79–1.97 (m, 4H), 3.63 (s, 2H), 3.71 (s, 3H), 3.76–3.83 (m, 2H), 7.09 (d, 1H, J=8 Hz), 7.20 (d, 1H, J=10 Hz).

EXAMPLE 9

Production of 4-[5-(4-acetoxytetrahydrofuran-3-yloxycarbonyl-methylthio)-4-chloro-2-fluorophenylimino]-3-thia-1,5-diaza-bicyclo[3.3.0]octan-2-one:

By using 5-[5-(4-acetoxytetrahydrofuran-3-yloxycarbonylmethylthio)-4-chloro-2-fluorophenylimino]-thiadiazolidin-2-one, the same procedure as in the above Example 7 was repeated, except for using 1,3-dibromopropane instead of 1,4-dibromobutane, to give the title compound having the following physical properties.

NMR (δ, CDCl$_3$): 2.05 (s, 3H), 2.61 (quint, 2H, J=7 Hz), 3.65 (s, 2H), 3.8 (m, 2H), 3.87 (t, 2H, J=7 Hz), 3.95 (t, 2H, J=7 Hz), 4.0 (m, 2H), 5.3 (m, 2H), 7.14 (d, 1H, J=8 Hz), 7.17 (d, 1H, J=10 Hz).

EXAMPLE 10

Production of 4-[4-chloro-2-fluoro-5-(methoxycarbonylmethyl-thio)phenylimino]-3-thia-1,5-diazabicyclo[3.3.0]octan-2-one:

By using 5-[4-chloro-2-fluoro-5-(metoxycarbonylmethylthio)phenylimino]-1,3,4-thiadiazolidin-2-one, the same procedure as in the above Example 7 was repeated, except for using 1,3-dibromopropane instead of 1,4-dibromobutane, to give the title compound having the following physical properties.

NMR (δ, CDCl₃): 2.60 (sept, 2H, J=7 Hz), 3.63 (s, 2H), 3.72 (s, 3H), 3.87 (t, 2H, J=7 Hz), 3.95 (t, 2H, J=7 Hz), 7.11 (d, 1H, J=8 Hz), 7.18 (d, 1H, J=10 Hz).

According to the process of the present invention, a 3,4-alkylene-1,3,4-thiadiazolidin-2-one, which is useful as a herbicide, can be easily produced in a high yield by using a 1,3,4-thiadiazolidin-2-one as a starting material.

While the invention has been described in detail and with reference to specific embodiments thereof, it will be apparent to one skilled in the art that various changes and modifications can be made therein without departing from the spirit and scope thereof.

What is claimed is:

1. A process for producing 3,4-alkylene-1,3,4-thiadiazolidin-2-one represented by the formula (III):

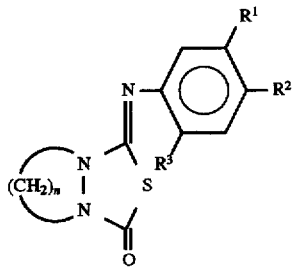
(III)

wherein R¹ represents a hydrogen atom or an inert substituent; R² represents a halogen atom, a nitro group, a methyl group or a methoxy group; R³ represents a hydrogen atom or a halogen atom; and n represents an integer of from 3 to 5, which comprises reacting a 1,3,4-thiadiazolidin-2-one represented by the formula (I):

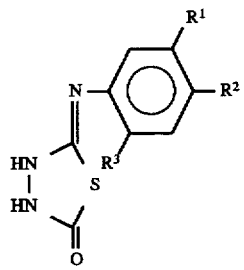
(I)

wherein R¹, R² and R³ are each as defined above, with a dihaloalkane represented by the formula (II):

X(CH₂)ₙX  (II)

wherein X represents a halogen atom; and n is as defined above, in the presence of a base.

2. A process as claimed in claim 1, wherein said 1,3,4-thiadiazolidin-2-one is obtained by hydrolyzing a 3-formyl-1,3,4-thiadiazolidin-2-one represented by the formula (IV):

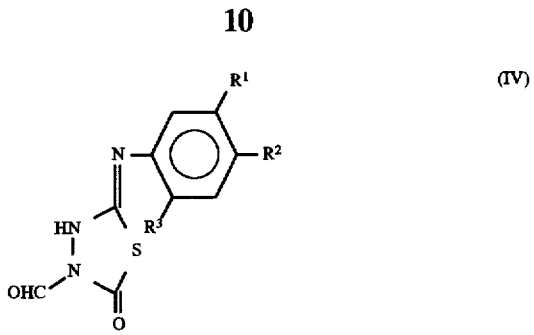
(IV)

wherein R¹, R² and R³ are each as defined in claim 1.

3. A process as claimed in claim 2, wherein said 3-formyl-1,3,4-thiadiazolidin-2-one is obtained by reacting a thiosemicarbazide represented by the formula (V):

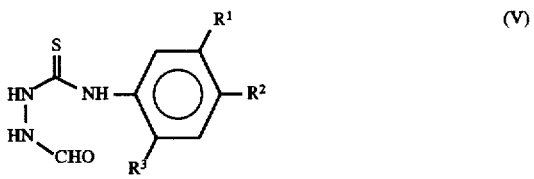
(V)

wherein R¹, R² and R³ are each as defined in claim 1, with phosgene.

4. A process as claimed in claim 3, wherein said thiosemicarbazide is obtained by reacting an isothiocyanate represented by the formula (VI):

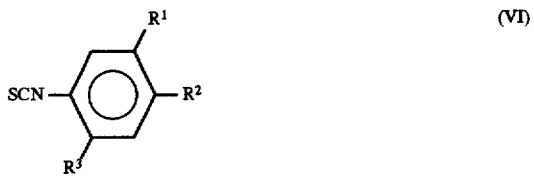
(VI)

wherein R¹, R² and R³ are each as defined in claim 1, with formhydrazide.

5. A process as claimed in claim 1, wherein R¹ is a group represented by —ACH₂CO₂R⁴, in which A is an oxygen atom or a sulfur atom and R⁴ is an alkyl group having 1 to 4 carbon atoms, a cycloalkyl group having 3 to 6 carbon atoms or a tetrahydrofuryl group substituted by an acyloxy group having 2 to 5 carbon atoms; R² is a halogen atom; R³ is a hydrogen atom or a halogen atom; and n is an integer of from 3 to 5.

6. A process as claimed in claim 2, wherein R¹ is a group represented by —ACH₂CO₂R⁴, in which A is an oxygen atom or a sulfur atom and R⁴ is an alkyl group having 1 to 4 carbon atoms, a cycloalkyl group having 3 to 6 carbon atoms or a tetrahydrofuryl group substituted by an acyloxy group having 2 to 5 carbon atoms; R² is a halogen atom; R³ is a hydrogen atom or a halogen atom; and n is an integer of from 3 to 5.

7. A process as claimed in claim 3, wherein R¹ is a group represented by —ACH₂CO₂R⁴, in which A is an oxygen atom or a sulfur atom and R⁴ is an alkyl group having 1 to 4 carbon atoms, a cycloalkyl group having 3 to 6 carbon atoms or a tetrahydrofuryl group substituted by an acyloxy group having 2 to 5 carbon atoms; R² is a halogen atom; R³ is a hydrogen atom or a halogen atom; and n is an integer of from 3 to 5.

8. A process as claimed in claim 4, wherein R¹ is a group represented by —ACH₂CO₂R⁴, in which A is an oxygen atom or a sulfur atom and R⁴ is an alkyl group having 1 to 4 carbon atoms, a cycloalkyl group having 3 to 6 carbon atoms or a tetrahydrofuryl group substituted by an acyloxy group having 2 to 5 carbon atoms; $R^2$ is a halogen atom; $R^3$ is a hydrogen atom or a halogen atom; and n is an integer of from 3 to 5.

9. A process as claimed in claim 1, wherein $R^1$ is a group represented by —$SCH_2CO_2R^4$, in which $R^4$ is a methyl group or a 4-acetoxytetrahydrofruan-3-yl group; $R^2$ is a chlorine atom; $R^3$ is a fluorine atom; and n is an integer of 3 or 4.

10. A process as claimed in claim 2, wherein $R^1$ is a group represented by —$SCH_2CO_2R^4$, in which $R^4$ is a methyl group or a 4-acetoxytetrahydrofruan-3-yl group; $R^2$ is a chlorine atom; $R^3$ is a fluorine atom; and n is an integer of 3 or 4.

11. A process as claimed in claim 3, wherein $R^1$ is a group represented by —$SCH_2CO_2R^4$, in which $R^4$ is a methyl group or a 4-acetoxytetrahydrofruan-3-yl group; $R^2$ is a chlorine atom; $R^3$ is a fluorine atom; and n is an integer of 3 or 4.

12. A process as claimed in claim 4, wherein $R^1$ is a group represented by —$SCH_2CO_2R^4$, in which $R^4$ is a methyl group or a 4-acetoxytetrahydrofruan-3-yl group; $R^2$ is a chlorine atom; $R^3$ is a fluorine atom; and n is an integer of 3 or 4.

* * * * *